United States Patent [19]

Markwell et al.

[11] Patent Number: 5,190,937
[45] Date of Patent: Mar. 2, 1993

[54] LACTAM DERIVATIVES

[75] Inventors: Roger E. Markwell; Ian Hughes, both of Harlow, England

[73] Assignee: Beecham Group p.l.c., Brentford, England

[21] Appl. No.: 640,069

[22] Filed: Jan. 11, 1991

[30] Foreign Application Priority Data

Jan. 15, 1990 [GB] United Kingdom ............... 9000846

[51] Int. Cl.$^5$ ............... C07D 225/02; C07D 223/10; A61K 31/55; A61K 31/395
[52] U.S. Cl. ............... 514/183; 514/212; 540/463; 540/524; 540/525; 540/527
[58] Field of Search ............... 514/212, 183; 540/463, 540/524, 525, 527

[56] References Cited

U.S. PATENT DOCUMENTS

| | | | |
|---|---|---|---|
| 4,587,050 | 5/1986 | Harris et al. | 540/463 |
| 4,734,410 | 3/1988 | Yanagisawa et al. | 540/463 |
| 4,831,135 | 5/1990 | Crews | 540/527 |
| 4,908,445 | 3/1990 | Rinehart | 540/527 |

FOREIGN PATENT DOCUMENTS 273689 7/1988 European Pat. Off. .
358305 3/1990 European Pat. Off. .

*Primary Examiner*—Mark L. Berch
*Attorney, Agent, or Firm*—Hopgood, Calimafde, Kalil, Blaustein & Judlowe

[57] ABSTRACT

Novel compounds of formula (I), and pharmaceutically acceptable salts thereof; their preparation; compositions containing them; and their use in the treatment of conditions in which degradation of connective tissue and other proteinaceous components of the body occurs:

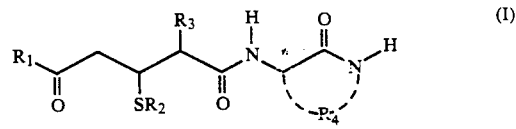

in which, $R_1$ is —OH; alkoxy; aryloxy or aralkyloxy in each of which the aryl group is optionally substituted; —$NR_6R_7$, where each of $R_6$ and $R_7$ is independently hydrogen or alkyl, or $R_6$ and $R_7$ together with the nitrogen atom to which they are bonded form a 5-, 6- or 7-membered ring with an optional oxygen or sulphur atom or an optionally substituted second nitrogen atom in the ring; or a group:

—NH—CH($R_8$)—C(O)—$R_9$ where $R_8$ is hydrogen; alkyl optionally substituted by —OH, alkoxy, —$NR_6R_7$ as defined for $R_1$, guanidine, —$CO_2H$, —$CONH_2$, —SH, or —S—alkyl; or —$CH_2$—Ar where Ar is optionally substituted aryl or heteroaryl; and $R_9$ is alkoxy; —OH; or —$NR_6R_7$ as defined for $R_1$; $R_2$ is hydrogen; $C_{2-8}$ alkanoyl; or optionally substituted aroyl; $R_3$ is $C_{3-6}$ alkyl; and $R_4$ is —($CH_2$)$_m$— where m is an integer from 4 to 12.

10 Claims, No Drawings

LACTAM DERIVATIVES

The present invention relates to novel thiol-carboxylic acid derivatives, processes for their preparation and their use in medicine. In particular, the present invention relates to their use as inhibitors of enzymes of the collagenase family of neutral metalloproteases, for treating arthritic and other diseases.

The mammalian collagenase family of enzymes comprises a number of proteases, exemplified by interstitial (type I) collagenase itself, the stromelysins (also known as proteoglycanases or transins), fibroblast and polymorphonuclear leucocyte gelatinases (also known as collagen-IV-ases), and 'pump-1' (putative metalloprotease 1, uterine metalloprotease) [Goldberg et al, J. Biol. Chem. 2610, 6600, 1986; Whitham et al, Biochem. J. 240, 913, 1986; Breathnach et al, Nucleic Acids Res., 15, 1139, 1987; Muller et al, Biochem. J., 253, 187, 1988; Collier et al, J. Biol. Chem., 263, 6579, 1988; Murphy et al., Biochem. J., 258, 463, 1989; Quantin et al, Biochem. (N.Y.), 28, 5327, 1989; Birkedal-Hansen, J. Oral Pathol., 17, 445, 1988]. Membership of the mammalian collagenase family of proteases is evident by possession of a number of highly characteristic and experimentally verifiable properties, which can be adopted as criteria for allocation to this family of enzymes, selected from the following:

(a) Optimal proteolytic activity around neutral pH.

(b) Dependence of the enzyme's activity on the presence of zinc, as evident by the loss of activity on treatment with divalent metal ion chelators, such as 1,10-phenanthroline (preferential chelation of zinc), or EDTA (less restricted chelating properties; EDTA and EGTA also contribute to enzyme inactivation via chelation of calcium ions required for enzyme stability.)

(c) Inhibition by TIMP (Tissue Inhibitor of Metalloproteinases), a proteinaceous inhibitor thought to play a significant role in the physiological control of the collagenase family of enzymes. Other families of metalloproteases are not inhibited by TIMP, at least as far as the relevant studies have so far been pursued.

(d) Absence of significant inhibition by known inhibitors of other families of neutral, zinc-containing metalloproteases, such as thermolysin, angiotensin-converting enzyme and 'enkephalinase' (EC 3.4.24.11). One of the inhibitors most often used is phosphoramidon, which inhibits thermolysin and enkephalinase.

(e) Biosynthesis and secretion as latent precursor forms (zymogens), requiring extracellular activation. Activation has been achieved by a number of endoproteases, organomercurials and chaotropic agents.

Members of the collagenase family of neutral metalloprotease enzymes have distinctive substrate specificities. Thus, collagenase type I itself is unique in its ability to cleave a specific peptide bond within the native fibrils of the interstitial collagens (e.g. types I, II and III). The o gelatinases are only poorly active on these collagens, but are able to degrade denatured interstitial collagens, as well as the non-fibrillar collagens, e.g. type IV, such as are found in the basement membrane. Pump-1 has been reported to act preferentially on denatured collagens (gelatins), though its profile differs from that of the stromelysins or the collagenases type IV. Both the stromelysins and the gelatinases are also capable of degrading non-collagenous structural proteins, such as elastin and the core protein of proteoglycan. Macromolecules involved in cell-to-substratum and cell-to-cell interactions, such as laminin and fibronectin, are also susceptible to degradation by several of these metalloproteases.

The range of therapeutic applications of the inhibitors of the collagenase family of enzymes described hereinafter reflects the fundamental role of these and other proteinaceous substrates of these enzymes in the connective tissue matrix throughout the body. Applications extend to clinical interventions in many diseases and phenomena not primarily due to a net destruction of collagen and other connective tissue components, but involving normal or disordered tissue remodelling.

Enzymes of the collagenase family are produced by synovial and skin fibroblasts, chondrocytes, peripheral mononuclear cells, keratinocytes and gingival tissue; related enzymes are also found within granular storage vesicles in polymorphonuclear leucocytes (PMNLs).

Inhibitors of the collagenase family of enzymes are considered to provide useful treatments for:

(i) arthritic diseases, such as rheumatoid and osteoarthritis, soft tissue rheumatism, polychondritis and tendonitis;

(ii) bone resorption diseases, such as osteoporosis, Paget's disease, hyperparathyroidism and cholesteatoma;

(iii) the enhanced collagen destruction that occurs in association with diabetes;

(iv) the recessive classes of dystrophic epidermolysis bullosa;

(v) periodontal disease and related consequences of gingival production of collagenase, or of PMNL collagenase release following cellular infiltration to inflamed gingiva, including by combating the greater susceptibility of diabetes patients to periodontal disease;

(vi) corneal ulceration, e.g. that induced by alkali or other burns, by radiation, by vitamin E or retinoid deficiency;

(vii) ulceration of the skin and gastro-intestinal tract, and abnormal wound healing;

(viii) post-operative conditions, including colonic anastomosis, in which collagenase levels are raised;

(ix) cancer, where members of the collagenase family of enzymes have been implicated in the neovascularization required to support tumour growth and survival, in the tissue remodelling required to accommodate the growing primary and secondary tumours, and in the penetration of tumour cells through the basement membrane of the vascular walls during metastasis;

(x) demyelinating diseases of the central and peripheral nervous systems, including syndromes in which myelin loss is the primary pathological event and those in which demyelination follows axonal atrophy. The degradation of myelin in these diseases, exemplified by multiple sclerosis, is mediated by members of the collagenase family of enzymes.

As a particular example of the therapeutic value of inhibitors of the collagenase family of enzymes such as are disclosed in the present invention, chronic arthritic diseases leading to extensive loss of the collagen, proteoglycan and elastin components of the cartilage, bone and tendons within the joints, should be amenable to treatment with inhibitors of the collagenases, proteoglycanases (stromelysins) and gelatinases currently thought to be the major enzymes involved.

These enzymes have been detected in extracts of synovial and cartilage tissue, and have also been extensively studied in tissue cultures of a wide range of connective tissues. Apart from control of the biosynthesis, secretion and activation of the enzymes, the most important natural regulation of these enzymes in normal and diseased states, is considered to be the endogenous production of inhibitors such as the Tissue Inhibitor of Metalloproteinases, and alpha-2 macroglobulin. An imbalance between the local levels of the proteolytic enzymes and of their natural inhibitors will allow destruction of connective tissue components to occur.

The compounds described in the present invention, being synthetic and low molecular weight inhibitors of this family of enzymes, offer a therapeutically useful way in which a more normal or non-pathological balance between inhibition and enzymic activity can be restored: they thus act to complement and supplement the endogenous enzyme inhibitors. Indeed, because these enzymes usually act only within restricted pericellular environments, before being inactivated by inhibitors circulating in the blood and present in most inflammatory exudates, the low molecular weight inhibitors disclosed here may be more effective than endogenous proteinaceous inhibitors that are excluded by their size from the localized regions of connective tissue destruction.

European Patent Publication 0273689 (Beecham Group) discloses a class of thiol-carboxylic acid derivatives having activity as inhibitors of collagenase and useful in the treatment of rheumatoid arthritis and related diseases in which collagenolytic activity is a contributing factor.

European Patent Publication 0276436 (Hoffmann-La Roche) discloses a class of phosphinic acid derivatives which inhibit the enzyme collagenase and are useful in the form of medicaments for the control or prevention of degenerative joint diseases such as rheumatoid arthritis and osteoarthritis.

A novel class of thiol-carboxylic acid derivatives has now been discovered, which are collagenase inhibitors and thus of potential utility in the treatment of diseases in which activity of members of the collagenase family of neutral metalloproteases is implicated.

According to the present invention there is provided a compound of general formula (I), or a pharmaceutically acceptable salt thereof:

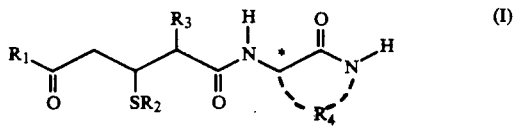

in which, $R_1$ is —OH: alkoxy; aryloxy or aralkyloxy in each of which the aryl group is optionally substituted; —$NR_6R_7$, where each of $R_6$ and $R_7$ is independently hydrogen or alkyl, or $R_6$ and $R_7$ together with the nitrogen atom to which they are bonded form a 5-, 6- or 7-membered ring with an optional oxygen or sulphur atom or an optionally substituted second nitrogen atom in the ring; or a group:

where $R_8$ is hydrogen; alkyl optionally substituted by —OH, alkoxy, —$NR_6R_7$ as defined for $R_1$, guanidine, —$CO_2H$, —$CONH_2$, —SH, or —S—alkyl; or —$CH_2$—Ar where Ar is optionally substituted aryl or heteroaryl; and $R_9$ is alkoxy; —OH; or —$NR_6R_7$ as defined for $R_1$; $R_2$ is hydrogen; $C_{2-8}$ alkanoyl; or optionally substituted aroyl; $R_3$ is $C_{3-6}$ alkyl; and $R_4$ is -($CH_2$)m- where m is an integer from 4 to 12.

Unless otherwise specified, each alkyl or alkoxy group is a $C_{1-8}$ group, more preferably a $C_{1-6}$ group, and may be straight chain or branched.

Values for aryl groups include naphthyl and phenyl, preferably phenyl. Values for heteroaryl groups include 5- or 6-membered monocyclic and 9- or 10-membered bicyclic heteroaryl which is preferred.

5- or 6-Membered monocyclic and 9- or 10-membered bicyclic heteroaryl groups preferably contain one or two heteroatoms selected from nitrogen, oxygen and sulphur which in the case of there being more than one heteroatom may be the same or different. A 9- or 10-membered bicyclic heteroaryl group preferably has a 5- or 6-membered ring containing a single heteroatom, for example indolyl. Optional substituents for aryl and heteroaryl groups may be selected from —OH, $C_{1-6}$ alkyl, $C_{1-6}$ alkoxy and halogen.

Where —$NR_6R_7$ is a heterocyclic ring containing a second nitrogen atom, suitable optional substituents include $C_{1-6}$ alkyl, for example methyl.

Values for $R_1$ include hydroxy; $C_{1-6}$ alkoxy, such as methoxy, ethoxy, propyloxy or butyloxy; benzyloxy; $C_{1-4}$ alkoxybenzyloxy such as 4-methoxybenzyloxy; and -$NR_6R_7$ in which $R_6$ is hydrogen, and $R_7$ is hydrogen or $C_{1-8}$ alkyl such as methyl or ethyl, or —$NR_6R_7$ is N'-methyl-N-piperazinyl or N-morpholinyl.

$R_1$ is preferably hydroxy; alkoxy, such as $C_{1-4}$ alkoxy, especially methoxy or isopropyloxy; or amino.

When $R_2$ is optionally substituted aroyl, the aroyl group is preferably a phenyl group, optionally substituted by —OH, $C_{1-6}$ alkyl, $C_{1-6}$ alkoxy or halogen.

Examples of $R_2$ are hydrogen and acetyl. Preferably $R_2$ is hydrogen.

$R_3$ is preferably a $C_4$ alkyl group, such as n-butyl, iso-butyl or sec-butyl, especially iso-butyl.

$R_4$ is preferably —($CH_2$)$_m$— where m is 10, forming part of a lactam structure based on a 13-membered ring.

The compounds of formula (I) may form salts with bases e.g. sodium hydroxide. When a basic nitrogen atom is present, the compounds of formula (I) may form acid addition salts e.g. with hydrochloric acid. Such compounds form part of the present invention.

Where compounds of formula (I), or pharmaceutically acceptable salts thereof, form solvates such as hydrates, these also form an aspect of the invention.

The compounds of formula (I) have at least three asymmetric centres and therefore exist in more than one stereoisomeric form. The invention extends to all such forms and to mixtures thereof, including racemates, and diastereoisomeric mixtures. Preferred isomers are those derived from the (−)-enantiomer of compounds of formula (VI) hereinafter described, which are believed to confer an S-configuration at the chiral centre marked with an asterisk in formula (I).

The compounds of formula I and their pharmaceutically acceptable salts are preferably in substantially pure form.

A substantially pure form will generally contain at least 50% by weight, preferably 75%, more preferably 90% and still more preferably 95% or 99% or more of the compound of formula I or its pharmaceutically acceptable salt.

One preferred pharmaceutically acceptable form is the crystalline form.

The present invention provides the compounds of formula (I) or pharmaceutically acceptable salts thereof for use as active therapeutic agents, particularly as agents for the treatment of musculo-skeletal disorders resulting from collagenolytic activity, particularly arthritic diseases, and for the modulation of tissue remodelling.

Compounds of formula (I) also have potential utility in the treatment of cancer; for preventing myelin degradation in the central and peripheral nervous system; and in other conditions in which members of the collagenase family of neutral metalloproteases have pathological or other roles.

The present invention also provides a process for the preparation of a compound of formula (I), which process comprises reacting a compound of formula (II):

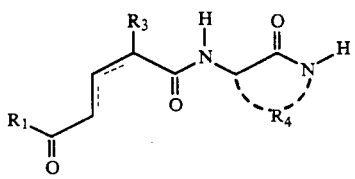

wherein $R_1$, $R_3$ and $R_4$ are as defined in formula (I), with a thiol of formula (III):

    (III)

wherein L is a conventional sulphur protection group, to give a compound of formula (IV):

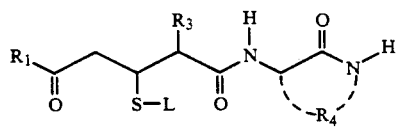

wherein $R_1$, $R_3$ and $R_4$ are as defined in formula (I) and L is as defined in formula (III); and thereafter, as necessary or desired, cleaving the group L and interconverting $R_1$.

Typically a sulphur protection group L is a substituted benzyl group, such as alkoxybenzyl, for example 4-methoxybenzyl, or an aliphatic or aryl acyl group such as acetyl or benzoyl. When L is an acyl group which is $C_{2-8}$ alkanoyl or optionally substituted aroyl, it is of course identical to $R_2$, so that compounds of formula (IV) in which $L=R_2$ are themselves compounds of the invention.

When L is a substituted benzyl sulphur protection group, such as 4-methoxybenzyl, then L may be removed by treatment with mercury acetate in trifluoroacetic acid containing anisole, followed by reaction with hydrogen sulphide in dimethylformamide, in a procedure analogous to that described in Chem. Pharm. Bull 1576, 26, (1978).

When L is an acyl group it may be removed by treatment with a base, for example aqueous ammonia or dilute aqueous sodium hydroxide, or by treatment with an acid, for example methanolic hydrochloric acid.

Other conventional methods for removing sulphur protection groups may also be used.

Intermediate compounds of formula (IV) can be converted to further compounds of formula (IV) while retaining the same group L, which group can in turn be cleaved to form compounds of the invention in which $R_2$ is hydrogen. Alternatively, interconversion of $R_1$ may be carried out after cleavage of the group L.

For example, those compounds of formula (I) in which $R_1$ is —OH may be prepared under acid or basic conditions by hydrolysis of compounds in which $R_1$ is alkoxy, aryloxy or aralkyloxy or by hydrogenolysis of compounds in which $R_1$ is benzyloxy or substituted benzyloxy in the presence of a catalyst such as palladium black. Basic hydrolysis is suitably carried out in aqueous alcohol in the presence of sodium hydroxide.

Compounds of formula (I) in which $R_1$ is alkoxy may be prepared from compounds in which $R_1$ is hydroxy by esterification. For example by treatment with an appropriate alcohol in the presence of an acid catalyst such as $BF_3$—$Et_2O$ (Synthesis, 316, 1972).

Those compounds of formula (I) in which $R_1$ is —$NR_6R_7$ may be prepared from compounds in which $R_1$ is —OH by treating the latter compounds with an amine of formula $NHR_6R_7$ in the presence of a coupling agent such as N,N-dicyclohexylcarbodiimide or N-ethyl-N'-dimethylaminopropylcarbodiimide.

Where both $R_6$ and $R_7$ are hydrogen, an $R_1$ hydroxyl group may be treated with chloroformate, for example ethyl chloroformate, followed by an excess of ammonia. Alternatively compounds in which $R_1$ is alkoxy, for example methoxy, may undergo aminolysis in an alcoholic solvent in the presence of sodium cyanide as catalyst, according to the procedure of T. Hogberg et al., (J.Org.Chem., 52, 2033, 1987).

Compounds of formula (I) in which $R_1$ is —NH—CH($R_8$)—C(O)$R_9$ may be similarly prepared from compounds in which $R_1$ is —OH by treatment with amine derivatives of formula $NH_2CH(R_8)C(O)R_9$ where $R_9$ is an alkoxy or amino group, followed by hydrolysis to give an $R_9$ hydroxy group, if desired.

In addition, intermediate compounds of formula (IV) in which L is an acyl group can be converted to compounds of the invention with interconversion of $R_1$ and concomitant cleavage of the acyl group to give compounds of formula (I) in which $R_2$ is hydrogen.

For example, those compounds of formula (I) in which $R_1$ is —OH and $R_2$ is hydrogen may be prepared by hydrolysis of compounds of formula (IV) in which $R_1$ is alkoxy, aryloxy or aralkyloxy and L is acyl, under basic conditions such as treatment with dilute sodium hydroxide.

The intermediate compounds of formula (II) may be prepared by treating a compound of formula (V):

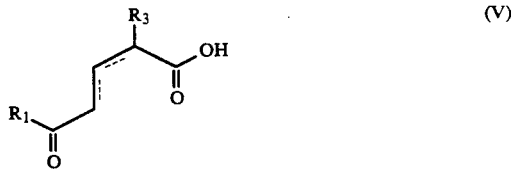

in which $R_1$ and $R_3$ are as defined in formula (I), with a compound of formula (VI):

wherein R₄ is as defined in formula (I).

The reaction is suitably carried out in the presence of a coupling agent, such as 1,1'-carbonyldiimidazole.

The 3-aminolactam compounds of formula (VI) are either known compounds or may be prepared from known starting materials by known methods. For example, the compound 3-amino-azacyclotridecan-2-one is prepared from commercially available 2-azacyclotridecanone by a procedure described in EP-A-0276436.

The thiols of formula (III) are known compounds.

Intermediate compounds of formulae (II) and (IV) disclosed herein are novel compounds and form an aspect of the present invention.

The preparation of certain compounds of formula (V) is described in EP-A-0273689.

Where obtainable, pharmaceutically acceptable salts of the compounds of formula (I) may be formed conventionally by reaction with the appropriate acid or base. Solvates may be formed by crystallization from the appropriate solvent.

As mentioned previously, the compounds of formula (I) exist in more than one diastereoisomeric form. Where the processes of the invention produce mixtures thereof, the individual isomers may be separated one from another by chromatography, e.g. HPLC.

Alternatively, separate diastereoisomeric compounds of formula (I) can be obtained by using stereoisomerically pure starting materials or by separating desired isomers of intermediates at any stage in the overall synthetic process, and converting these intermediates to compounds of formula (I).

It will be appreciated that although the absolute configuration at a particular chiral centre may not be known, it is possible to characterise a given diastereoisomer relative to its epimer by reference to the direction in which the plane of polarised light is rotated.

The present invention further provides a pharmaceutical composition, which comprises a compound of formula (I), or a pharmaceutically acceptable salt thereof, and a pharmaceutically acceptable carrier.

A composition of this invention is useful in the treatment of musculo-skeletal disorders, particularly arthritic diseases and for the modulation of tissue remodelling.

A composition of the invention, which may be prepared by admixture, may contain a diluent, binder, filler, disintegrant, flavouring agent, colouring agent, lubricant or preservative in conventional manner. These conventional excipients may be employed in conventional manner, for example as in the preparation of compositions of related peptide enzyme inhibitors, such as the ACE inhibitor captopril.

A composition of the invention may be adapted for oral, topical, rectal or parenteral administration but oral administration is preferred. Parenteral compositions may be administered intravenously, intramuscularly or intra-articularly.

Preferably, a pharmaceutical composition of the invention is in unit dosage form and in a form adapted for use in the medical or veterinarial fields. For example, such preparations may be in a pack form accompanied by written or printed instructions for use as an agent in the treatment or prophylaxis of any of the disorders mentioned above.

The suitable dosage range for the compounds of the invention may vary from compound to compound and may depend on the condition to be treated. It will also depend, inter alia. upon the relation of potency to absorbability and the mode of administration chosen.

The compound or composition of the invention may be formulated for administration by any route, the preferred route depending upon the disorder for which treatment is required, and is preferably in unit dosage form or in a form that a human patient may administer to himself in a single dosage.

Compositions may, for example, be in the form of tablets, capsules, sachets, vials, powders, granules, lozenges, reconstitutable powders, or liquid preparations, for example solutions or suspensions, or suppositories.

The compositions, for example those suitable for oral administration, may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable wetting agents such as sodium lauryl sulphate.

Solid compositions may be obtained by conventional methods of blending, filling, tabletting or the like. Repeated blending operations may be used to distribute the active agent throughout those compositions employing large quantities of fillers. When the composition is in the form of a tablet, powder, or lozenge, any carrier suitable for formulating solid pharmaceutical compositions may be used, examples being magnesium stearate, starch, glucose, lactose, sucrose, rice flour and chalk. Tablets may be coated according to methods well known in normal pharmaceutical practice, in particular with an enteric coating. The composition may also be in the form of an ingestible capsule, for example of gelatin containing the compound, if desired with a carrier or other excipients. For example, a hard gelatin capsule containing the required amount of a compound of the invention in the form of a powder or granulate in intimate mixture with a lubricant, such as magnesium stearate, a filler, such as microcrystalline cellulose, and a disintegrant, such as sodium starch glycollate.

Compositions for oral administration as liquids may be in the form of, for example, emulsions, syrups, or elixirs, or may be presented as a dry product for reconstitution with water or other suitable vehicle before use. Such liquid compositions may contain conventional additives such as suspending agents, for example sorbitol, syrup, methyl cellulose, gelatin, hydroxyethylcellulose, carboxymethylcellulose, aluminium stearate gel, hydrogenated edible fats; emulsifying agents, for example lecithin, sorbitan monooleate, or acacia; aqueous or non-aqueous vehicles, which include edible oils such as almond oil and fractionated coconut oil, oily esters, for example esters of glycerine, propylene glycol, ethyl alcohol, glycerine, water or normal saline; preservatives, for example methyl or propyl p-hydroxybenzoate or sorbic acid; and if desired conventional flavouring or colouring agents.

The compounds of this invention may also be administered by a non-oral route. In accordance with routine pharmaceutical procedure, the compositions may be formulated, for example for rectal administration as a suppository or for parenteral administration in an injectable form. For injection, for example by intra-articular injection or by injection into the cerebro-spinal fluid or via other routes which will gain access to sites of demyelination, as freely soluble solutions or as poorly dispersed depot stores, the compounds of the invention may be presented in an aqueous or non-aqueous solution, suspension or emulsion in a pharmaceutically acceptable liquid, e.g. sterile pyrogen-free water or a parenterally acceptable oil or a mixture of liquids, which may contain bacteriostatic agents, anti-oxidants or other preservatives, buffers or solutes to render the solution isotonic with the blood, thickening agents, suspending agents or other pharmaceutically acceptable additives. Such forms will be presented in sterile unit dose form such as ampoules or disposable injection devices or in multi-dose forms such as a bottle from which the appropriate dose may be withdrawn or a solid form or concentrate which can be used to prepare an injectable formulation.

For topical and percutaneous administration, the preparations may also be presented as an ointment, cream, lotion, gel, spray, aerosol, wash, skin paint or patch.

A unit dose for treating diseases and for modulating physiological phenomena in which enzymes from the collagenase family are involved will generally contain from 10 to 1000 mg and preferably will contain from 10 to 500 mg, in particular 10, 50, 100, 150, 200, 250, 300, 350, 400, 450 or 500 mg. The composition may be administered once or more times a day, for example 2, 3 or 4 times daily, so that the total daily dose for a 70 kg adult will normally be in the range 10 to 3000 mg. Such a dose corresponds to approximately 0.15 to 50 mg/kg per day. Alternatively, in particular for injection, the unit dose will contain from 2 to 20 mg of a compound of the invention and be administered in multiples, if desired, to give the desired daily dose.

The present invention additionally provides a method of treating conditions in which degradation of connective tissue and other proteinaceous components of the body occurs, such as rheumatism and/or arthritic conditions in mammals, such as humans, which comprises administering to the mammal in need of such treatment an effective amount of a compound of formula (I) or a pharmaceutically acceptable salt thereof.

The present invention also provides the use of a compound of formula (I) or a pharmaceutically acceptable salt thereof, for the manufacture of a medicament for use in the treatment of conditions in which degradation of connective tissue and other proteinaceous components of the body occurs such as rheumatism and/or arthritic conditions.

The following Description and Examples illustrate the preparation of compounds of the invention.

DESCRIPTION 1

6-Methyl-4-[(2-oxoazacyclotridec-3-yl)-aminocarbonyl]-hept-2(and 3)-enoic acids, methyl esters (D1)

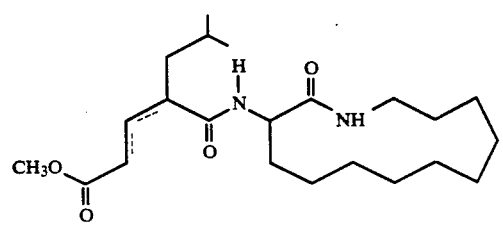

A solution of 4-methoxycarbonyl-2-(2-methylpropyl)-but-2-enoic acid (prepared as in EP-A-273689) (10.0 g, 0.05 mol) in dry acetonitrile (100 ml) under nitrogen was cooled to 0° C. in an ice bath and then treated with 1,1'-carbonyldiimidazole (11.13 g, 0.069 mol) in one portion. After 1 h at 0° C. (−)-3-amino(azacyclotridecan-2-one) (12.2 g; 0.057 mol) [[α]$_D^{20}$= −63.6° (c=1% in methanol)] was added and the solution was stirred at 0° C. for 1 h, and then at room temperature overnight. The reaction mixture was evaporated to dryness in vacuo and then dissolved in ethyl acetate (1 liter) and washed with 10% sodium carbonate solution (x2), water, and finally dried over anhydrous sodium sulphate. The product was subjected to flash-column chromatography on silica gel 60 (40–63 μM) (500 g) (see W. C. Still et al., *J. Org. Chem.*, 1978, 43, 2923), using ethyl acetate-pentane (1:1) as eluent to give the title compound (D1) as a solid (11.5 g), m.p. 130°–133° C. after trituration with ether-pentane (1:1). (Found: C,66.95; H,9.73; N,6.92. $C_{22}H_{38}N_2O_4$ requires C,66.97; H,9.71; N,7.10%).

EXAMPLE 1

3-Acetylmercapto-6-methyl-4-[(2-oxoazacyclotridec-3-yl)aminocarbonyl]heptanoic acid, methyl ester (E1)

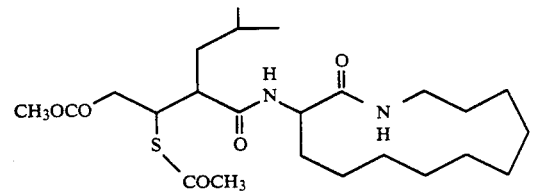

A solution of 6-methyl-4-[(2-oxoazacyclotridec-3-yl)aminocarbonyl]hept-2(and 3)-enoic acids, methyl esters (D1) (11.3 g) in thiolacetic acid (130 ml) was set aside at room temperature for 12 days and then evaporated to dryness in vacuo. The product was subjected to flash-column chromatography on silica gel 60 (400 g) using hexane, followed by ether-hexane (1:1), as the eluent. The first solid fractions eluted from the column were combined (3.8 g) and recrystallised from ethyl acetate-pentane to afford the title compound (E1A) (0.55 g), m.p. 213°–216° C. as a single diastereoisomer. Found: C,61.41; H,9.04; N,5.98. $C_{24}H_{42}N_2O_5S$ requires C,61.25; H,8.99; N,5.95%). δ (CDCl$_3$) 0.85 (6H,d,J=6 Hz), 1.2–1.9 (21H,br.m), 2.33 (3H,s), 2.7 (3H,m), 2.85 (1H,m), 3.68 (3H,s), 3.8 (1H,m), 3.95 (1H,m), 4.45 (1H,m), 6.15 (1H,br.d) and 6.58 (1H,d,J=8 Hz). m/z 470. $C_{24}H_{42}N_2O_5S$ requires M 470.

The mother-liquors from the above recrystallization were combined with later column fractions and triturated with ether to afford a further quantity (1.6 g) of the title compound, (E1A).

EXAMPLE 2

3-Mercapto-6-methyl-4-(2-oxoazacyclotridec-3-yl)aminocarbonyl]heptanoic acid, methyl ester (E2)

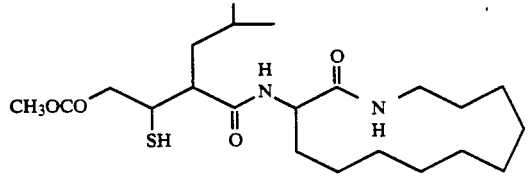

An ice-cooled solution of 3-acetylmercapto-6-methyl- 4-[2-oxoazacyclotridec-3-yl)aminocarbonyl]heptanoic acid, methyl ester (E1) (0.51 g) in nitrogen-purged methanol (200 ml) was treated with 35% aqueous ammonia (50 ml), and the reaction mixture was stirred under nitrogen for 2 h and then evaporated to dryness in vacuo. The product was chromatographed on silica gel 60 (70 g) using ethyl acetate-chloroform (1:1) as the eluent. The product was triturated with ether and then pentane to give the title compound (E2A) (0.4 g), m.p. 223°-228° C. as a single diastereoisomer. (Found: C,61.93; H,9.49; N,6.68. $C_{22}H_{40}N_2O_4S$ requires C,61.65; H,9.41; N,6.54%).

δ (CDCl$_3$) 0.88 (6H,m), 1.2-1.95 (21H,m), 1.9 (1H,d,J=8 Hz), 2.55 (2H,m), 2.8 (2H,m), 3.3 (1H,m), 3.7 (3H,s), 3.8 (1H,m), 4.47 (1H,m), 6.15 (1H,br.s) and 6.7 (1H,brd,J=8 Hz).

m/z 428. $C_{22}H_{40}N_2O_4S$ requires M 428; $[\alpha]_D^{20}$ = $-49.5°$(c=1% in CHCl$_3$).

When the above procedure was repeated with a sample of 3-acetylmercapto-6-methyl-4-[2-oxoazacyclotridec-3-yl)amino carbonyl]heptanoic acid methyl ester (E1) (0.93 g) containing about 25% of a co-eluting diastereoisomer, concentration of the mother-liquors after recrystallizing the product from ethyl acetate-ether, afforded the title compound as a 1:1 mixture of two diastereoisomers (E2A and E2B) (0.25 g).

δ (CDl$_3$) 0.88 (6H, m), 1.2-1.85 (21H, m), 1.90 (0.5H, d, J=8 Hz), 1.95 (0.5H, d, J=8 Hz), 2.45-2.65 (2H, m), 2.7-2.9 (2H, m), 3.1-3.4 (1H, m), 3.70 (s), 3.71 (s) and 3.8 (m) (total 4H), 4.47 (1H, m), 5.5 (1H, br.s), 6.5 (1H, br.t) and 6.82 (1H, br.t).

In a different experiment, when a mixture of diastereoisomers of 3-mercapto-6-methyl-4-[(2-oxoazacyclotridec-3-yl)aminocarbonyl]heptanoic acid, methyl ester (E2) (0.58 g) was chromatographed on silica gel 60 with ethyl acetate-chloroform (1:2) as the eluent, a fraction was isolated (0.3 g) containing a mixture of two diastereoisomers (E2 A/C) in a ratio of 4:5. The mixture was separated by preparative HPLC [250×10 mm Rainin Microsorb C18 column; flow rate 6 ml/min; acetonitrile-water (45:55); retention times—E2A 31.25 min and E2C 30.36 min] to give the title compound as a single diastereoisomer (E2C), m.p. 191°-194° C.

δ (CD$_3$OD) 0.88 (3H, d, J=7 Hz), 0.92 (3H, d, J=7 Hz), 1.25-1.55 (17H, m), 1.63 (2H, m), 1.75 (2H, m), 2.47 (1H, dd, J=9, 16 Hz), 2.62 (1H, m), 2.82 (1H, m), 2.88 (1H, dd, J=4, 16 Hz), 3.25 (1H, m), 3.62 (1H, m), 3.69 (3H, s) and 4.32 (1H, br.t, J=7 Hz).

EXAMPLE 3

3-Mercapto-6-methyl-4-[(2-oxoazacyclotridec-3-yl)aminocarbonyl]heptanoic acid (E3)

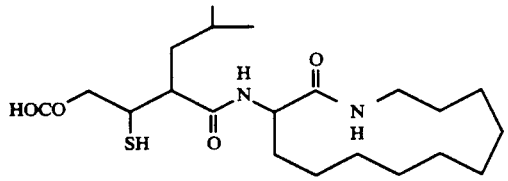

To a suspension of 3-mercapto-6-methyl-4-[(2-oxoazacyclotridec-3 yl)aminocarbonyl]heptanoic acid, methyl ester (E2A) (1.03 g) in isopropanol (15 ml), previously purged with nitrogen, was added a solution of sodium hydroxide (0.29 g) in water (5 ml) and the resulting solution was stirred at room temperature, under nitrogen, for 18 h. The solution was acidified with an excess of ethereal-HCl and then evaporated to dryness in vacuo. The residue was treated with isopropanol and then evaporated to dryness in vacuo.

A portion of the product was washed well with water and dried in vacuo to give the title compound as a single diastereoisomer (E3A), m.p. 226°-229° C. Found: C,60.57; H,9.24; N,6.71%. $C_{21}H_{38}N_2O_4S$ requires C,60.84; H,9.24; N,6.76%.

δ (CD$_3$OD) 1.02 (6H, t, J=6 Hz), 1.35-1.9 (21H, m), 2.55 (1H, dd, J=15, 10 Hz), 2.67 (1H, m), 2.84 (1H, dd, J=15, 3 Hz), 2.92 (1H, m), 3.3 (1H, m), 3.75 (1H, m) and 4.42 (1H, m).

Observed FAB (M+H)$^+$415. $C_{21}H_{38}N_2O_4S$ requires M 414. The crude product was used without further purification in the preparation of Example 4.

EXAMPLE 4

3-Mercapto-6-methyl-4-(2-oxoazacyclotridec-3-yl)aminocarbonyl]heptanoic acid, isopropyl ester (E4)

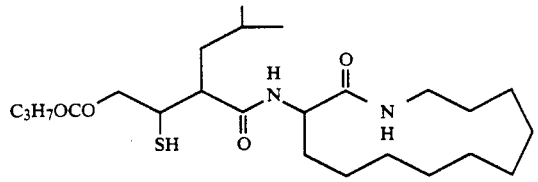

A solution of 3-mercapto-6-methyl-4-[azacyclotridec-3-yl)aminocarbonyl]heptanoic acid (E3) (crude product from Example 3) in isopropanol (40 ml) under nitrogen was treated with boron trifluoride-etherate (5 ml) and then heated at 70° C. for 24h. Water (1 ml) was added cautiously, and then the solution was evaporated to dryness in vacuo. The residue was dissolved in chloroform, washed with water, brine, dried (Na$_2$SO$_4$),and evaporated to dryness in vacuo. The product was chromatographed on silica gel (20 g) eluting with chloroform-pentane (1:1) and finally chloroform-ethyl acetate (9:1) to give the title compound as a single diastereoisomer (E4A), (0.70 g), (after trituration with ether m.p. 208°-215° C. (Found: C,63.3; H,9.83; N,6.08. $C_{24}H_{44}N_2O_4S$ requires C,63.12; H,9.71; N,6.13%.

$[\alpha]_D^{20}$= −48.1 (c 0.98% in CHCl$_3$).

δ (CDCl$_3$) 0.89 (3H, d, J=6 Hz), 0.90 (3H, d, J=6 Hz), 1.2-1.90 (21H, m), 1.88 (1H, d, J=8 Hz), 2.52 (1H, m), 2.52 (1H, dd, J=10, 16 Hz), 2.77 (1H, dd, J=3, 16 Hz), 2.85 (1H, m), 3.31 (1H, m), 3.79 (1H, m), 4.48 (1H, m), 5.06 (1H, m), 6.3 (1H, m) and 6.71 (1H, br.d, J=8 Hz).

Observed CI (M+H)$^+$457. $C_{24}H_{44}N_2O_4S$ requires M 456.

EXAMPLE 5

3-Mercapto-6-methyl-4-(2-oxoazacyclotridec-3-yl)aminocarbonyl]heptanamide (E5)

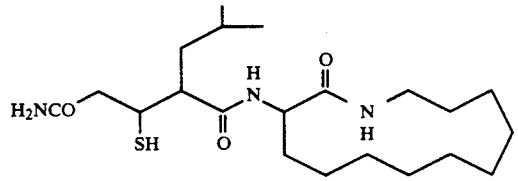

A solution of 3-mercapto-6-methyl-4-[(2-oxoazacyclotridec-3-yl)aminocarbonyl]heptanoic acid, methyl ester (E2A) (50 mg) was heated in nitrogen-purged-methanol (10 ml) containing liquid ammonia (ca 5 ml) and sodium cyanide (10 mg) at 70° C. for 18 h in a sealed vessel. The reaction mixture was evaporated to dryness in vacuo and chromatographed on silica gel 60 (50 g). Elution with ethyl acetate, followed by methanol-ethyl acetate (1:9) gave the title compound (15 mg) as a single diastereoisomer (E5A), m.p. 240°-255° C. (dec.).

Observed FAB (M+H)+414. $C_{21}H_{39}N_3O_3S$ requires M 413.

COLLAGENASE INHIBITOR ASSAY

The test is performed essentially as in Cawston and Barrett, Anal. Biochem. 99, 340-345 (1979). Compounds for testing are dissolved in methanol by sonication and added to collagenase (purified from culture supernatants from the human lung fibroblast cell line, WI-38) in buffer. To ensure that thiol collagenase inhibitors remain unoxidised, β-mercaptoethanol may be incorporated in the methanol solvent and/or the diluent buffers to give a final concentration of $9.6 \times 10^{-5}M$. The minimal direct effect of β-mercaptoethanol on the degradation of collagen by human collagenase is controlled for. After a 5 min pre-incubation at 37° C., the assay tubes are cooled to 4° C. and $^3H$-acetylated rat skin type I collagen is added. The assay tubes are incubated at 37° C. overnight. The $^3H$-collagen forms insoluble fibrils, which are the substrate for the enzyme.

To terminate the assay, the assay tubes are spun at 12000 rpm for 15 min. Undigested $^3H$-collagen is pelleted, while digested $^3H$-collagen is found as soluble peptides in the supernatant. A sample of the supernatant is taken for liquid scintillation counting.

The activity of collagenase inhibitors ($IC_{50}$:50% inhibitory concentration) is expressed as that concentration of compound that inhibits a known (standard) concentration of enzyme by 50%.

The activities of representative compounds of the invention, in the above test procedure, are illustrated in the table below:

| Inhibition of human lung fibroblast collagenase | |
|---|---|
| Example No. | $IC_{50}$ (M) |
| E1A | $2.8 \times 10^{-8}$ |
| E2A | $2.7 \times 10^{-9}$ |
| E3A | $7.45 \times 10^{-8}$ |
| E4A | $1.5 \times 10^{-8}$ |

We claim:
1. A compound of formula (I) or a pharmaceutically acceptable salt thereof:

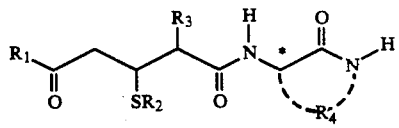

in which, $R_1$ is
—OH; alkoxy; aryloxy or aralkyloxy in each of which the aryl group is optionally substituted by a member selected from the group consisting of —OH, $C_{1-6}$ alkyl, $C_{1-6}$ alkoxy and halogen;
—$NR_6R_7$, where each of $R_6$ and $R_7$ is independently hydrogen or alkyl, or $R_6$ and $R_7$ together with the nitrogen atom to which they are bonded form a 5-, 6-, or 7-membered ring with an optional oxygen or sulphur atom or a second nitrogen atom in the ring, said optional second nitrogen atom optionally substituted by $C_{1-6}$ alkyl;
or a group —NH—CH($R_8$)—C(O)—$R_9$ where $R_8$ is hydrogen; alkyl optionally substituted by —OH, alkoxy, —$NR_6R_7$ as defined for $R_1$, guanidine, —$CO_2H$, —$CONH_2$, —SH, or —S—alkyl; or —$CH_2$—Ar where Ar is optionally substituted aryl or heteroaryl, wherein heteroaryl is selected from aromatic heterocyclic compounds having a 5- or 6-membered monocyclic ring or a 9-membered fused bicyclic aromatic heterocyclic group containing one or two nitrogen atoms, the optional substituents being selected from the group consisting of —OH, $C_{1-6}$ alkyl, $C_{1-6}$ alkoxy and halogen; and $R_9$ is alkoxy; —OH; or —$NR_6R_7$ as defined for $R_1$;

$R_2$ is hydrogen; $C_{2-8}$ alkanoyl; or aroyl optionally substituted by —OH, $C_{1-6}$ alkyl, $C_{1-6}$ alkoxy or halogen;

$R_3$ is $C_{3-6}$ alkyl; and $R_4$ is —$(CH_2)_m$— where m is an integer from 4 to 12.

2. A compound according to claim 1, in which $R_1$ is hydroxy; $C_{1-4}$ alkoxy; or amino.

3. A compound according to claim 1 in which $R_2$ is hydrogen or acetyl.

4. A compound according to claim 1 in which $R_3$ is n-butyl, iso-butyl or sec-butyl.

5. A compound according to claim 1 in which $R_4$ is —$(CH_2)_m$— where m is 10.

6. A compound according to claim 1 in which $R_1$ is hydroxy, methoxy, isopropyloxy or amino; $R_2$ is hydrogen; $R_3$ is iso-butyl; and $R_4$ is —$(CH_2)_m$— where m is 10.

7. A compound selected from the group comprising:
3-acetylmercapto-6-methyl-4-[(2-oxoazacyclotridec-3-yl)aminocarbonyl]heptanoic acid, methyl ester;
3-mercapto-6-methyl-4-[(2-oxoazacyclotridec-3-yl)aminocarbonyl]heptanoic acid, methyl ester;
3-mercapto-6-methyl-4-[(2-oxoazacyclotridec-3-yl)aminocarbonyl]heptanoic acid;
3-mercapto-6-methyl-4-[(2-oxoazacyclotridec-3-yl)aminocarbonyl]heptanoic acid, isopropyl ester; and
3-mercapto-6-methyl-4-[(2-oxoazacyclotridec-3-yl)aminocarbonyl]heptanamide.

8. A pharmaceutical composition comprising a compound of formula (I) as defined in claim 1, or a pharmaceutically acceptable salt thereof, and a pharmaceutically acceptable carrier.

9. A method of treating rheumatic and/or arthritic conditions, which method comprises administering to a mammal in need of such treatment an effective amount of a compound of formula (I) as defined in claim 1 or a pharmaceutically acceptable sale thereof.

10. A compound of formula (IV):

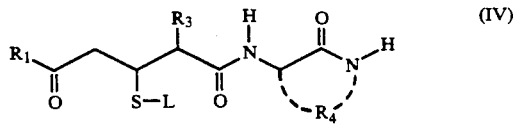

in which $R_1$ is
—OH; alkoxy; aryloxy or aralkyloxy in each of which the aryl group is optionally substituted by a member selected from the group consisting of —OH, $C_{1-6}$ alkyl, $C_{1-6}$ alkoxy and halogen;

—$NR_6R_7$, where each of $R_6$ and $R_7$ is independently hydrogen or alkyl, or $R_6$ and $R_7$ together with the nitrogen atom to which they are bonded form a 5-, 6-, or 7-membered ring with an optional oxygen or sulphur atom or a second nitrogen atom in the ring, said optionally second nitrogen atom optionally substituted by $C_{1-6}$ alkyl;

or a group —NH—CH($R_8$)—C(O)—$R_9$ where $R_8$ is hydrogen; alkyl optionally substituted by —OH, alkoxy, —$NR_6R_7$ as defined for $R_1$, quanidine, —$CO_2H$, —$CONH_2$, —SH, or —S—alkyl; or —$CH_2$—AR where Ar is optionally substituted aryl or heteroaryl, wherein heteroaryl is selected from aromatic heterocyclic compounds having a 5- or 6-membered monocyclic ring or a 9-membered fused bicyclic aromatic heterocyclic group containing one or two nitrogen atoms, the optional substituents being selected from the group consisting of —OH, $C_{1-6}$ alkyl, $C_{1-6}$ alkoxy and halogen; and $R_9$ is alkoxy; —OH; or —$NR_6R_7$ as defined for $R_1$;

$R_3$ is $C_{3-6}$ alkyl;

$R_4$ is —$(CH_2)_m$— where m is an integer from 4 to 12; and

L is a conventional sulfur protecting group, provided that L is not $C_{2-8}$ alkanoyl or optionally substituted aroyl.

* * * * *